United States Patent
Falk et al.

(10) Patent No.: US 9,872,807 B2
(45) Date of Patent: Jan. 23, 2018

(54) MULTIPLE PATIENT INFANT WARMING DEVICE, MANAGER AND METHOD

(71) Applicant: General Electric Company, Schenectady, NY (US)

(72) Inventors: Steven Mitchell Falk, Baltimore, MD (US); Lawrence Guy Ten Eyck, Ellicott City, MD (US); Marjorie Chappelle McCue, New Market, MD (US); Karen P. Starr, Monkton, MD (US)

(73) Assignee: General Electric Company, Schenectady, NY (US)

( * ) Notice: Subject to any disclaimer, the term of this patent is extended or adjusted under 35 U.S.C. 154(b) by 835 days.

(21) Appl. No.: 14/145,564

(22) Filed: Dec. 31, 2013

(65) Prior Publication Data
US 2015/0182406 A1    Jul. 2, 2015

(51) Int. Cl.
| | |
|---|---|
| *A61G 11/00* | (2006.01) |
| *A61F 7/10* | (2006.01) |
| *G06F 19/00* | (2011.01) |
| *G05D 23/19* | (2006.01) |
| *A61F 7/00* | (2006.01) |

(52) U.S. Cl.
CPC ............... *A61G 11/00* (2013.01); *A61F 7/10* (2013.01); *G05D 23/1934* (2013.01); *G06F 19/3406* (2013.01); *A61F 2007/0086* (2013.01); *A61F 2007/0088* (2013.01); *A61F 2007/0093* (2013.01); *A61F 2007/0096* (2013.01); *A61G 2203/20* (2013.01); *A61G 2203/44* (2013.01); *A61G 2203/46* (2013.01)

(58) Field of Classification Search
CPC ............ A61G 11/00; A61G 2203/46; A61G 2203/20; A61G 2203/44; A61F 7/10; A61F 2007/0096; A61F 2007/0093; A61F 2007/0086; A61F 2007/0088
See application file for complete search history.

(56) References Cited

U.S. PATENT DOCUMENTS 5,415,618 A * 5/1995 Koch ..................... A61G 11/00
                                                                      600/22
5,944,651 A * 8/1999 Koch ..................... A61G 11/00
                                                                      600/22
(Continued)

OTHER PUBLICATIONS

Lyon et al. Temperature Control in Preterm Infants-Effects of Birthweight and Gestational Age, pp. 83-91 (1995).*
(Continued)

*Primary Examiner* — Christine H Matthews
*Assistant Examiner* — Kaylee Wilson
(74) *Attorney, Agent, or Firm* — Andrus Intellectual Property Law, LLP

(57) ABSTRACT

A multiple patient infant warming management system comprises at least one temperature sensor for sensing at least one temperature of an infant warming device and a controller. The controller processes first signals for different temperature ranges of different temperature zones assigned to different patients to be concurrently warmed the infant warming device, receives second signals from the at least one temperature sensor indicating at least one temperature of the infant warming device and outputs adjustments based on the first signals and the second signals.

27 Claims, 8 Drawing Sheets

(56) References Cited

U.S. PATENT DOCUMENTS

| | | | |
|---|---|---|---|
| 6,953,427 B1 * | 10/2005 | Mackin | A61G 11/00 600/22 |
| 2003/0197003 A1 | 10/2003 | Kneuer | |
| 2007/0114292 A1 | 5/2007 | Breed et al. | |
| 2009/0177257 A1 | 7/2009 | Khodak et al. | |

OTHER PUBLICATIONS

International Search Report and Written Opinion for PCT/US2014/055763, dated Feb. 12, 2015, 12 pages.

* cited by examiner

MULTIPLE PATIENT INFANT WARMING DEVICE, MANAGER AND METHOD

BACKGROUND

Infant warming devices are sometimes utilized to maintain infant homeostasis. During shortages of such infant warming devices, multiple infants of different size and/or gestational age may cohabitate a single infant warming device.

DETAILED DESCRIPTION OF THE EXAMPLE EMBODIMENTS

Figure 1:
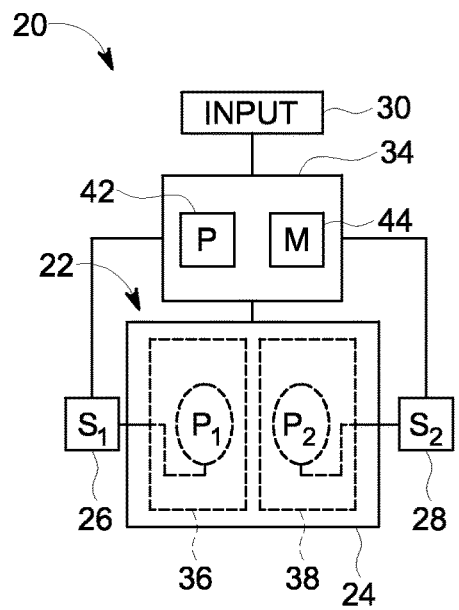
FIG. 1 is a schematic diagram of an example multi-patient infant warming device management system.

FIG. 1 schematically illustrates an example multi-patient infant warming device management system 20. Infant warming device management system may be provided as part of an infant care station, an infant warmer, an incubator, a hybrid warmer/incubator or other patient care stations in which multiple cohabitating infants are to be concurrently warmed. Infant warming device management system manages temperature zones for concurrently warming multiple infants/patients cohabitating a single warming crib or chamber. As will be described hereafter, infant warming device management system manages the temperature zones to reduce a likelihood of the multiple patients being concurrently warmed in incompatible manners.

Multi-patient infant warming device management system 20 comprises an infant warming device 22 comprising a warming chamber 24, sensors 26, 28, input 30 and controller 34. Warming chamber 24 comprises a warming crib, bed, compartment or other at least partially contained or surrounded volume in which multiple infant patients P1, P2 are to cohabitate while being concurrently warmed. Warming chamber 24 comprises regions or zones 36, 38 in which the cohabitating infant patients P1 and P2 are to rest while being concurrently warmed. In one implementation, zones 36, 38 are independent of one another. In another implementation, zones 36, 38 overlap one another. In one implementation, the size of each of zones as well the shape of each of zones 36, 38 may vary depending upon characteristics of the individual infant patients P1 and P2 residing therein. In one implementation, each of zones 36, 38 is demarcated within chamber 24 by a short dividing wall, markings, different mattresses, different colors or the like. In another implementation, zones 36, 38 are unmarked, omit marked boundaries and are indistinguishable from one another; each zone 36, 38 constituting a varying or indeterminate portion of the collective open space within chamber 24 that surrounds the particular patient P1, P2.

Sensors 26, 28 comprise sensing devices configured and located to sense temperature values that indicate or that may be used to derive one or more internal temperatures within chamber 24. In one implementation, sensor 26 comprises one or more sensors configured to indicate an internal temperature of zone 36 and/or patient P1 (as schematically indicated by broken lines connecting sensor 26 to patient P1), or to sense other temperature values may be used to derive the temperature of zone 36 and/or the temperature of patient P1. Sensor 28 comprises one or more sensors configured to indicate an internal temperature of zone 36 and/or patient P1 (as schematically indicated by broken lines connecting sensor 28 to patient P2), or to sense other temperature values may be used to derive the temperature of zone 38 and/or patient P2. In one implementation, sensors 26, 28 comprise sensors mounted to a wall of chamber 24 or other structure proximate interior of chamber 24. In yet another implementation, sensors 26, 28 comprise temperature sensing probes attachable to one or more regions of the anatomy of each of patients P1 and P2. Sensors 26, 28 output signals that are used by controller 34 to manage the temperature of zones 36, 38.

Input 30 comprises one or more devices by which commands, selections and/or data may be entered or input to controller 34. In the example illustrated, input 30 facilitates the input of information or parameters pertaining to patients P1, P2 such as age, weight, size, conditions current health conditions or status and the like. In some implementations, input 30 may be omitted.

Controller 34 is configured to analyze data and generate control signals for controlling and managing the operation of heaters, a display, an alarm and/or other output devices associated with warming chamber 24 and management system 20. Controller 34 comprises processor or processing unit 42 and associated memory 44. Processing unit 42 comprises one or more processing units configured to follow instructions contained in memory 44 to analyze data and generate control signals. For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 34 may be embodied as part of one or more application-specific integrated circuits (ASICs). Unless otherwise specifically noted, the controller is not limited to any specific combination of hardware circuitry and software, nor to any particular source for the instructions executed by the processing unit.

Memory 44 comprises a non-transitory computer-readable medium containing computer-readable instructions, software or code to direct processing unit 42 to carry out operations for the management of warming device 22. In one implementation, memory 44 contains computer-readable instructions for directing system 20 to carry out method 100 illustrated in FIG. 2. As indicated by step 120 of method 100, processing unit 42 of controller 34, following instructions contained in memory 44, processes first signals for different temperature ranges of different temperature zones 36, 38 assigned to different patients P1, P2, respectively. Such temperature ranges assigned to different temperature zones may be wide or may be very narrow. In one implementation, the range may be narrow so as to encompass a single temperature.

In one implementation, the different temperature ranges of different temperature zones 36, 38 that are assigned to the different patients P1, P2 are input through input 30 and stored in memory 44. For example, a care person may input a temperature range for patient P1 that is different than the temperature range for patient P2. In another implementation, the different temperature ranges of different temperature zones 36, 38 that are assigned to different patients P1, P2 are calculated or determined by controller 34 based upon receive signals indicating one or more parameters for patients P1, P2 such as the weight, age, size, health condition of the like for each of patients P1, P2. In one implementation, controller 34 may additionally or alternatively base the determination of the particular temperature range for each of patients P1, P2 based upon sensed data such as weight, blood oxygen saturation ($SPO_2$) or other sensed values for other parameters.

Figure 2:
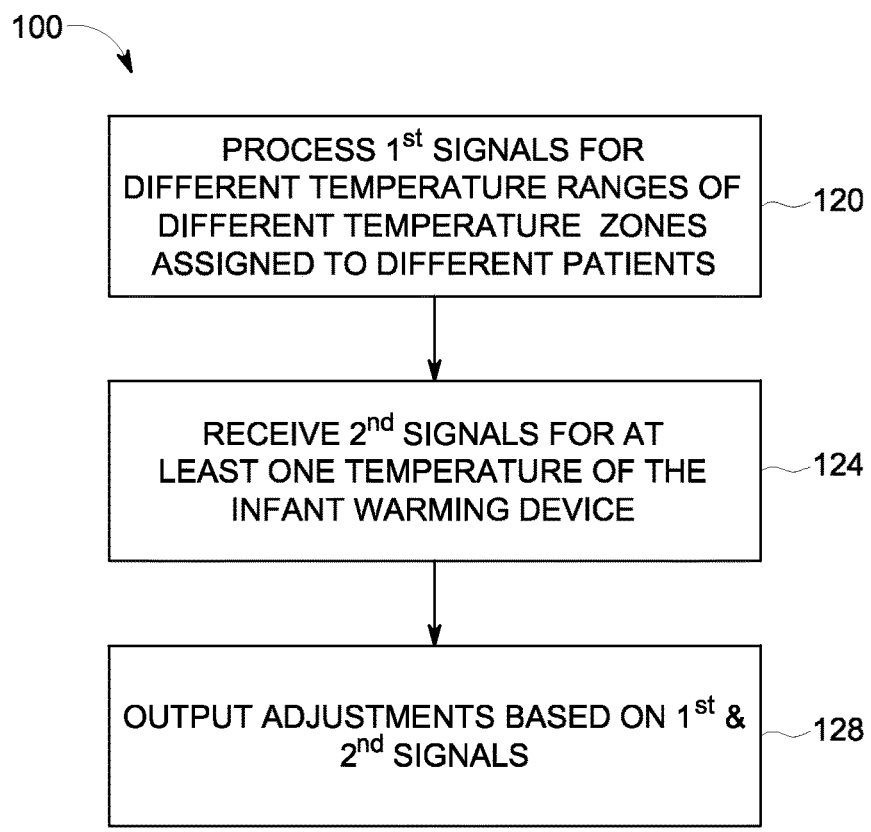
FIG. 2 is a flow diagram of an example method that may be carried out by the system of FIG. 1.

As indicated by step 124 of FIG. 2, processing unit 42 of controller 34, following instructions contained in memory 44, further receives second signals from sensors 26, 28 for at least one temperature associated with warming chamber 24 of infant warming device 22. In one implementation, processing unit 42 receives signals indicating a current temperature value for each of the individual temperature zones 36, 38. In another implementation, processing unit 42 receives signals from sensors 26, 28 indicating a single temperature for the interior of warming chamber 24 of warming device 22. In such implementations, one of sensors 26, 28 may be omitted. In some implementations, greater than two of such sensors 26, 28 may be provided as part of management system 20.

As indicated by step 128 of FIG. 2, processing unit 42, following instructions contained in memory 44, outputs adjustments based upon the first signals and the second signals. In one implementation, the output adjustments comprise control signals that modify operation of an audible or visible alarm/notification device, a display or other device that communicates a notice or message to a care person. In one implementation, the output adjustments comprise control signals that cause data, notifications, instructions and/or alarms (collectively referred to as a "message" or "messages") to be communicated to a display screen of the local monitor, to a server across a wired or wireless network that makes the message available on a website or to one or more other portable electronic devices, such as a smart phone, tablet computer, flash memory player, laptop or other device in communication with the server across the wired or wireless network, or directly to such a portable electronic device. In one implementation, the message notifies the care person of an incompatibility between the sensed temperature or temperatures within warming chamber 24 and the assigned temperature ranges for each of temperature zones 36, 38 assigned to patients P1 and P2, respectively. In another implementation, the message may alternatively or additionally provide instructional recommendations to the care person for adjustment of the operation of warming device 22.

In one implementation, the output adjustments comprise control signals that adjust the operation of warming chamber 24. For example, in one implementation, the output adjustments comprise control signals that adjust the operation of one or more heating devices associated with either or both of the internal temperature zones 36, 38 of warming chamber 24. For example, such control signals may cause one or more heating devices to output a greater amount of heat or a lesser amount of heat. In one implementation, the output adjustments comprise control signals that adjust the operation of one or more ventilation or cooling devices associate with either or both of the internal temperature zones 36, 38 of warming chamber 24. For example, such control signals may increase or decrease one or more fans, increase or decrease one or more cooling devices and/or open or close one more ventilation windows (in the case of a warming chamber that is enclosed) to a greater extent or lesser extent.

In one implementation, the internal area or volume of temperature zone 36 may be associated with a fan, a heat discharge window and/or a heat absorbing or cooling device. In circumstances where the other temperature zone, zone 38 has a higher assigned temperature range as compared to the temperature range assigned to temperature zone 36, such control signals may increase a cooling impact of the fan, the heat discharge window and/or the heat absorbing device such that system 20 may provide zone 38 with the higher assigned temperature while zone 36 is cooled to the lower temperature satisfying the lower assigned temperature for zone 36.

In a similar manner, temperature zone 38 may also be associated with a second fan, a second heat discharge window and/or a second heat absorbing or cooling device. In circumstances where the other temperature zone, zone 38 has a higher assigned temperature range as compared to the temperature range assigned to temperature zone 36, such control signals may increase a cooling impact of the second fan, the second discharge window and/or the second heat absorbing or cooling device such that system 20 may provide zone 38 with the higher assigned temperature while zone 36 is cooled to the lower temperature satisfying the lower assigned temperature range for zone 36.

In one implementation, warming chamber 24 may be associated with a plurality of independently actuatable or controllable heating devices such that heat output to temperature zone 36 may be different than the heat output to temperature zone 38. In one implementation, each temperature zone 38 within warming device 24 may have one or more associated or designated heating devices. In such an implementation, the output adjustments comprise control signals that independently control the heating devices such that temperature zones 36, 38 are heated to and maintained that temperatures that satisfy the assigned different temperature ranges for zone 36, 38. In one implementation, both cooling devices (fan, heat discharge window, heat absorbing devices) and heating devices may be independently and selectively controlled such that the temperatures of zones 36, 38 satisfy the different temperature ranges assigned to zones 36, 38.

In the example illustrated in FIG. 1, controller 34, input 30 and sensors 26, 28 are each part of the infant warming device 22 in that such components are contained within a single housing while sharing processing and memory resources. In another implementation, input 30 and controller 34 may be provided as part of a separate management unit that communicates with warming device 22, wherein warming device 22 provides sensors 26, 28. In another implementation, controller 34 may be provided as part of a separate management unit that communicates with warming device 22, wherein warming device 22 provides sensors 26, 28 and input 30. In each of the implementations in which controller 34 is remote from warming device 22, controller 34 may communicate with warming device 22 using appropriate transceivers for transmitting signals across a wired or wireless local area network or wide area network such as the Internet. In another implementation, memory 44 containing the computer-readable instructions for processor 42 is located remote from processing unit 42 and warming device 22. For example, memory 44 may alternatively reside in a remote server or a remote computing device that communicates with processing unit 42 of warming device 22 in a wired or wireless fashion either directly or across a local area network or a wide area network such as the Internet.

Figure 3:
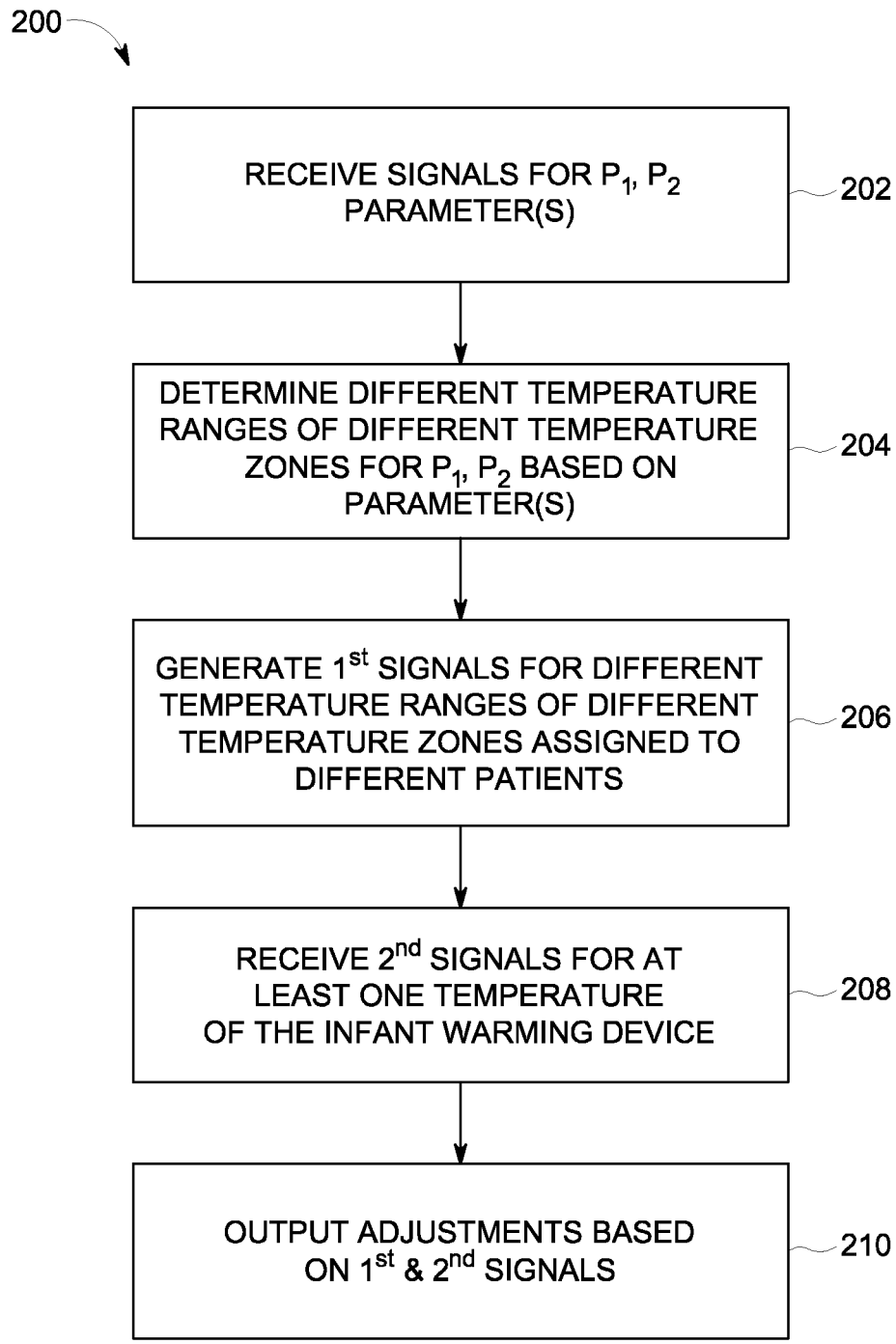
FIG. 3 is a flow diagram of another example method that may be carried out by the system of FIG. 1.

FIG. 3 is a flow diagram illustrating another method 200 for being carried out by system 20 of FIG. 1. As with method 100, method 200 facilitates the management of an infant warming device in which multiple patients are concurrently warmed. As indicated by step 202, controller 34 receive signals for one or more parameters of each of patients P1, P2. Examples of parameters include the weight, oxygen blood saturation (SPO2) and health conditions or characteristics of each patient. The signals corresponding to or indicating such parameters may be received as a result of (a) the input of such parameters through input 30 (whether local to infant warming device 22 or remote from infant warming device 22); (b) the retrieval of such parameters from a memory, such as memory 44, wherein memory 44 may be local to infant warming device 22 or may be remote from infant warming device 42 (accessed across a local area network or a wide area network such as the Internet); and/or (c) sensed by one or more sensors 26, 28.

As indicated by step 204, controller 34 determines or prescribes a temperature range for each of the different temperature zones 36, 38 assigned to each of the different patients P1, P2 based upon the one of more values represented by the parameter signals. Controller 34 determines a temperature range for temperature zone 36 based upon parameters associated with patient P1 and determines a different temperature range for temperature zone 38 based upon parameters associated with patient P2. In one implementation, controller 34 may determine that patient P1, based upon the age, weight, blood saturation level and/or health condition of patient P1, requires a first temperature range while patient P2, based upon the age, weight, blood saturation level and health condition of patient P2, requires a second different temperature range. In one implementation, such determination occurs during upon or shortly after the placement of patients P1 and P2 in warming chamber 24. In another implementation, such determination occurs on a periodic basis at predefined intervals or continuously occurs automatically in response to feedback received from sensors 26, 28 indicating changes to one or more of weight, blood saturation level and/or health conditions of either patient P1, P2.

As indicated by step 206, upon determining the different temperature ranges for the different temperature zones for patients P1, P2, processing unit 42 of controller 34 generates first signals for the different temperature ranges of the different temperature zones assigned to the different patients P1, P2. In one implementation, such signals result in the storage of the different temperature ranges for the different temperature zones assigned to the different patients P1, P2 in memory 44 or other memories.

As indicated by step 208, controller 34 receives second signals from sensors 26, 28 for the current temperature of receives second signals from sensors 26, 28 for at least one temperature associated with warming chamber 24 of infant warming device 22. In one implementation, processing unit 42 receives signals indicating a current temperature value for each of the individual temperature zones 36, 38. In another implementation, processing unit 42 receives signals from sensors 26, 28 indicating a single temperature for the interior of warming chamber 24 of warming device 22. In such implementations, one of sensors 26, 28 may be omitted. In some implementations, greater than two of such sensors 26, 28 may be provided as part of management system 20. As indicated by step 210, as in step 128, controller 34 outputs adjustments based upon the first and second signals.

Figure 4:
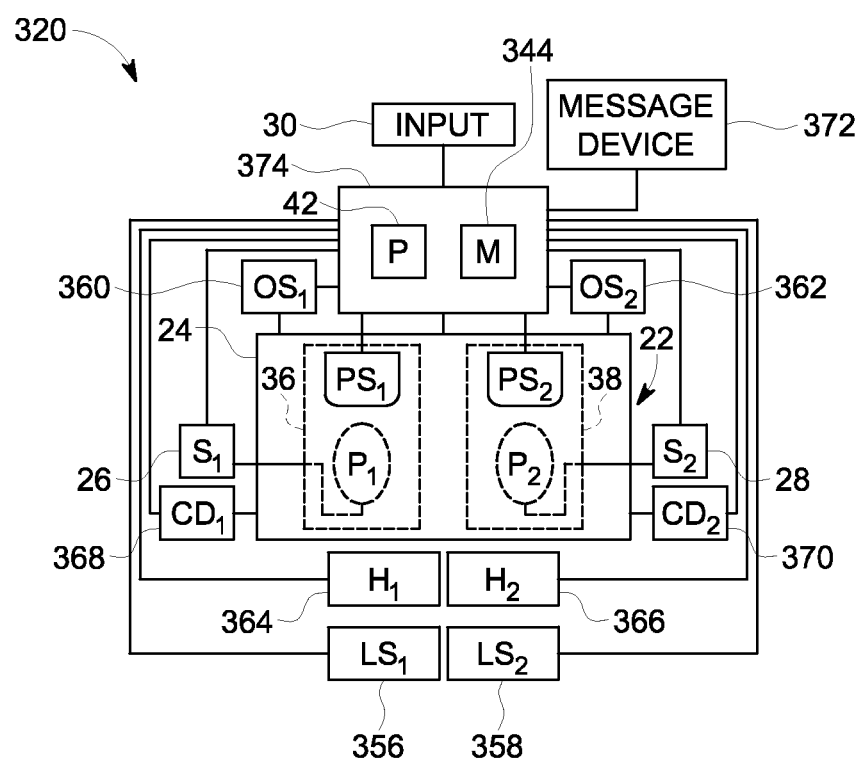
FIG. 4 is a schematic diagram of another example multi-patient infant warming device management system.

FIG. 4 schematically illustrates multi-patient infant warming device management system 320, another example implementation of multi-patient infant warming device management system 20. As with system 20, system 320 manages temperature zones for concurrently warming multiple infants/patients cohabitating a single warming crib or chamber to reduce a likelihood of the multiple patients being concurrently warmed in incompatible manners. System 320 comprises an infant warming device 22 comprising infant warming chamber 24, sensors 26, 28 and input 30, each of which is described above with respect to system 20. As shown by FIG. 4, system 320 is illustrated as specifically additionally comprising load sensors 356, 358, optical sensors 360, 362, heating devices 364, 366, cooling devices 368, 370, message device 372 and controller 374.

Load sensors 356, 358 comprise sensors located in configured to sense or detect weight or weight changes within warming chamber 24 of warming device 22. In one implementation, load sensors 356, 358 are located and configured to detect a number of patients within warming chamber 24. In one implementation, load sensors 356, 358 are further located and configured to output signals that facilitate the detection of particular positioning or location of the patients P1, P2 within warming chamber 24 to facilitate more refined temperature control of zones 36, 38 with respect to patients P1, P2, respectively. In one implementation, load sensors 356, 358 are further configured to output signals that facilitate the determination of the individual weight of each of patients P1, P2.

In one implementation, load sensors 356, 358 are located below the uppermost surface upon which patients P1, P2 rest, such as within or below a mattress upon which patients P1, P2 rest. Although system 320 is schematically illustrated as including two of such load sensors 356, 358, one load sensor dedicated for each general temperature zone 36, 38, in other implementations, system 320 may include more than two load sensors when infant warming chamber 24 is sized to possibly receive more than two patients. In one implementation, system 320 may include multiple load sensors for each general temperature zone 356, 358 or may include an undesignated array of load sensors 356, 358 spread across the reasons of zones 36, 38. In one implementation, such load sensors may be omitted.

Optical sensors 360, 362 comprise cameras, infrared or other optical emitter-detector detectors, or other optical sensing devices that are located with respect to warming chamber 24 and configured to optically detect the presence and/or positioning of patients within warming chamber 24. Optical sensors 360, 362 output signals that a used to determine the number of patients P1, P2 within warming chamber 24. In one implementation, such optical sensors 360, 362 output signals that further facilitate the determination of the precise positioning of patients P1, P2 within warming chamber 24 to facilitate more refined temperature control of zones 36, 38 with respect to patients P1, P2, respectively. In some implementations, optical sensors 360, 362 may be omitted.

Heating devices 364, 366 comprise devices to generate and/or apply heat to warming chamber 24. In one implementation, heating devices 364, 366 are independently adjustable to differently apply heat to temperature zones 36, 38. For example, in one operational setting, heating device 364 may apply a first amount of heat to temperature zone 36 while heating device 366 applies a second different amount of heat to temperature zone 38. In another implementation, heating device 364 may be closer proximity to temperature zone 36 or may be aimed or directed at temperature zone 36, while heating device 366 is in closer proximity to temperature zone 38 or may be aimed or directed at temperature zone 38. In another implementation, heating devices 364, 366 may alternatively be configured to apply heat to warming chamber 24 in an undirected or unbiased manner. Although system 320 is schematically illustrated as comprising a pair of heating devices 364, 366, in other implementations, system 320 may include a single heating device or may include greater than two heating devices.

Cooling devices 368, 370 comprise structures or devices to lower the temperature of temperature zones 36, 38, respectively. In one implementation, each of cooling devices 368, 370 is independently controllable or independently adjustable such that a temperature of temperature zone 36 may be lowered differently than the temperature of temperature zone 38. Cooling devices 368, 370 allow the one or more heating devices 364, 366 to heat warming chamber 24 to an overall desired upper temperature, wherein cooling devices 368, 370 selectively and differently cool the individual temperature zone 36, 38 to different temperatures to accommodate different temperature requirements for patients P1, P2. For example, in one circumstance, patient P2 may have a higher recommended warming temperature as compared to patient P1. In such a circumstance, warming chamber 24 may be warmed by heater 364, 366 to the higher temperature recommended for patient P2, wherein temperature zone 36 containing patient P1 may be cooled by cooling device 368 to the recommended lower temperature for patient P1.

In one implementation, cooling devices 368, 370 comprise fans or blowers configured to direct heat away from their associated temperature zone 36, 38. In such an implementation, control signals from controller 374 adjust the rotational speed or angular direction of the fans or blowers to independently vary the cooling impact of cooling devices 368, 370. In another implementation, such as when heating chamber 24 is a contained or enclosed environment, cooling devices 368, 370 comprise heat discharge windows or ports, allowing heat within an associated temperature zone 36, 38 to escape from warming chamber 24. In such an implementation, control signals from controller 374 adjust the number of openings and/or the size of such openings to independently adjust the extent of cooling in each of temperature zones 36, 38. In another implementation, cooling zone 368, 370 comprise heat absorbing devices that absorb heat within their associated temperature zone 36, 38. In such an implementation, control signals from controller 374 adjust the extent to which the heat absorbing devices absorb heat to independently adjust the extent of cooling each of temperature zones 36, 38.

Although system 320 is illustrated as comprising two cooling device 368, 370, in other implementations, system 320 may comprise a single cooling device which is either movable or which is adjustable to vary the cooling of one of temperature zones 36, 38 relative to the other of temperature zones 36, 38. In yet other implementations, system 320 may comprise greater than two cooling devices. Although system 320 is illustrated as utilizing both heating devices 364, 366 and cooling devices 368, 370 to adjust the temperature of temperature zones 36, 38 independent of one another, in other implementations, system 320 may omit cooling devices 368, 370 while using heating devices 364, 366 two provide independent heating of temperature zones 36, 38. Alternatively, heating devices 364, 366 heat warming chamber 24 to a uniform overall temperature, wherein cooling device 368, 370 provide the different temperatures of temperature zones 36, 38.

Message device 372 comprises a device to output a message which may comprise instructions, recommendations, alerts or alarms or other notifications. In one implementation, message device 372 outputs at least one of visible text and/or graphics, audible words, visible alarms, such as flashing lights and the like, and audible alarms, such as audible beeps or other sounds. In one implementation, message device 372 comprises a display screen, such as a display screen provided by a monitor associated with the infant warming device 22. In one implementation, message device 372 comprises a display screen of a computing device in direct communication with controller 374 through a wired connection or a wireless connection. In one implementation, device 372 comprises a display screen of the computing device in indirect communication with controller 374 through a local area network or a wide area network, such as the Internet. In one implementation, device 372 comprises a display screen of a portable electronic device in communication with controller 374. Examples of portable electronic devices include, but are not limited to, tablet computers, notebook computers, smart phones, flash memory players, personal data assistants and the like. In other implementations, device 372 comprises a speaker or a light emitting device of a control panel, computing device or a portable electronic device in communication with controller 374.

Controller 374 is similar to controller 34 of system 20 (described above) in that controller 374 is configured to analyze data and generate control signals for controlling and managing the operation of infant warming device 22. Controller 34 comprises processor or processing unit 42 (described above) and associated memory 344.

Memory 344 comprises a non-transitory computer-readable medium containing computer-readable instructions, software or code to direct processing unit 42 to carry out operations for the management of warming device 22. In one implementation, memory 344 contains computer-readable instructions for directing system 320 to carry out method 400 illustrated in FIG. 5. As indicated by block or step 402 of FIG. 5, processor 42, on instructions provided by memory 344, retrieves and/or receives signals for values of one or more parameters associated with patients residing in warming chamber 24. In the example illustrated, processing unit 42 of controller 374 retrieves a receives signals from load sensors 356, 358 and/or optical sensors 360, 362. Based upon such signals, processing unit 42, following instructions contained in memory 344, determines the number of patients within warming chamber 24.

For example, in one implementation, based upon a calibration weight (the weight of warming chamber 24 prior to receiving any infants) and the timing of the addition of weight to warming chamber 24, processing unit 42 may determine the number of patients. In another implementation in which warming chamber 24 includes an array of individual load sensors, processing unit 42, following instructions data memory 344, determines a number of patients within warming chamber 24 based upon load distribution across the array of individual load sensors, wherein load sensors between each patient may output signals indicating a much lower load as the patient does not directly overlie and press upon such sensors.

In another implementation, following instructions contained memory 344, processing unit 42 determines the number of patients within warming chamber 24 based upon signals from optical sensors 360, 362. In one implementation, controller 374 utilizes image analysis of digitized pixels to identify the presence or absence of an infant patient. In another implementation in which optical sensors 360, 362 comprise light emitter detector type sensors, the presence of an infant patient may interrupt and infrared or other light beam, wherein the absence of a patient would not interrupt and infrared or other light beam. In some implementations, controller 374 (processor 42 following instructions contained in memory 344) may determine the number of patients within warming chamber 24 utilizing signals from both load sensor 356, 358 and optical sensors 360, 362.

In some implementations, controller 374 may additionally determine the current positioning and size of each patient within warming chamber 24, wherein controller 374 utilizes the determined current positioning and size of each patient to define the location, size and/or shape of each temperature zone 36, 38 for each patient P1, P2. For example, different patients may have different sizes, shapes and may have various positions within warming chamber 24 such that the patient may not necessarily be centered within a standard or predefined temperature zone within chamber 24. Using the determined location, size and/or shape of each temperature zone 36, 38, controller 374 reformulates new temperature zone boundaries or adjusts standard temperature zone boundaries, generating control signals adjusting the output of heating devices 364, 366 and/or cooling devices 368, 370 to focus the heating and/or cooling impacts of such devices 364, 366, 368, 370 onto the adjusted temperature zones a better fit the actual patients within warming chamber 24.

In circumstances where warming chamber 24 is not receiving a maximum number of patients, such as a circumstance where warming chamber 24 is capable of receiving two patient but is only receiving an individual patient or where warming chamber 24 is capable of receiving three patients but is only receiving one or two patients, such patients may not necessarily be located at centered positions within a predefined temperature zone. For example, two patients may share the space having three available predefined temperature zones, wherein one or both of the patients extend across two temperature zones. In such circumstances, controller 374 is configured to identify the precise positioning of such patients, even when such patients may concurrently extend across two predefined temperature zones. Using the precise determined positioning of the individual patients, controller 374 redefines or adjusts the temperature zones so as to better match the actual shape an actual positioning of the patients, wherein controller 374 further generates control signals adjusting the output or aim of heating devices 364, 366 and/or cooling device 368, 370 based upon the redefined or adjusted temperature zones.

In addition to receiving sensed signals indicating the presence or absence of a patient within a region of warming chamber 24, controller 374 may additionally receive signals from other sensors indicating values of other parameters. For example, controller 374 may additionally receive signals indicating the weight or changes in weight of an individual patient P1, P2. In one implementation, weight indicating signals may be received from load sensors 356, 358. In one implementation, controller 374 may additionally receive signals indicating blood oxygen saturation levels ($SPO_2$) from sensors position on each of patients P1, P2. In other implementations, controller 374 may receive other signals from sensors indicating values for other parameters of each of patients P1, P2.

The signals received by controller 374 in step 402 may additionally or alternatively comprise signals that indicate or represent data retrieved from a memory or database, such as memory 344 or generated as a result of care person input through input device 30. In one implementation, processing unit 42, following instructions contained memory 344, may retrieve data (in the form of signals) from an external database whether local to warming device 22 or remote from warming device 22 such as from a memory across a local area network or a wide area network. Such signals retrieved by controller 374 may indicate a health condition of each of the patients received within warming chamber 24, the gestational age of each of patients received within warming chamber 24, a length or height of each of such patients or other special circumstances which may impact the temperature to which each patient should be warmed or maintained.

Figure 5:
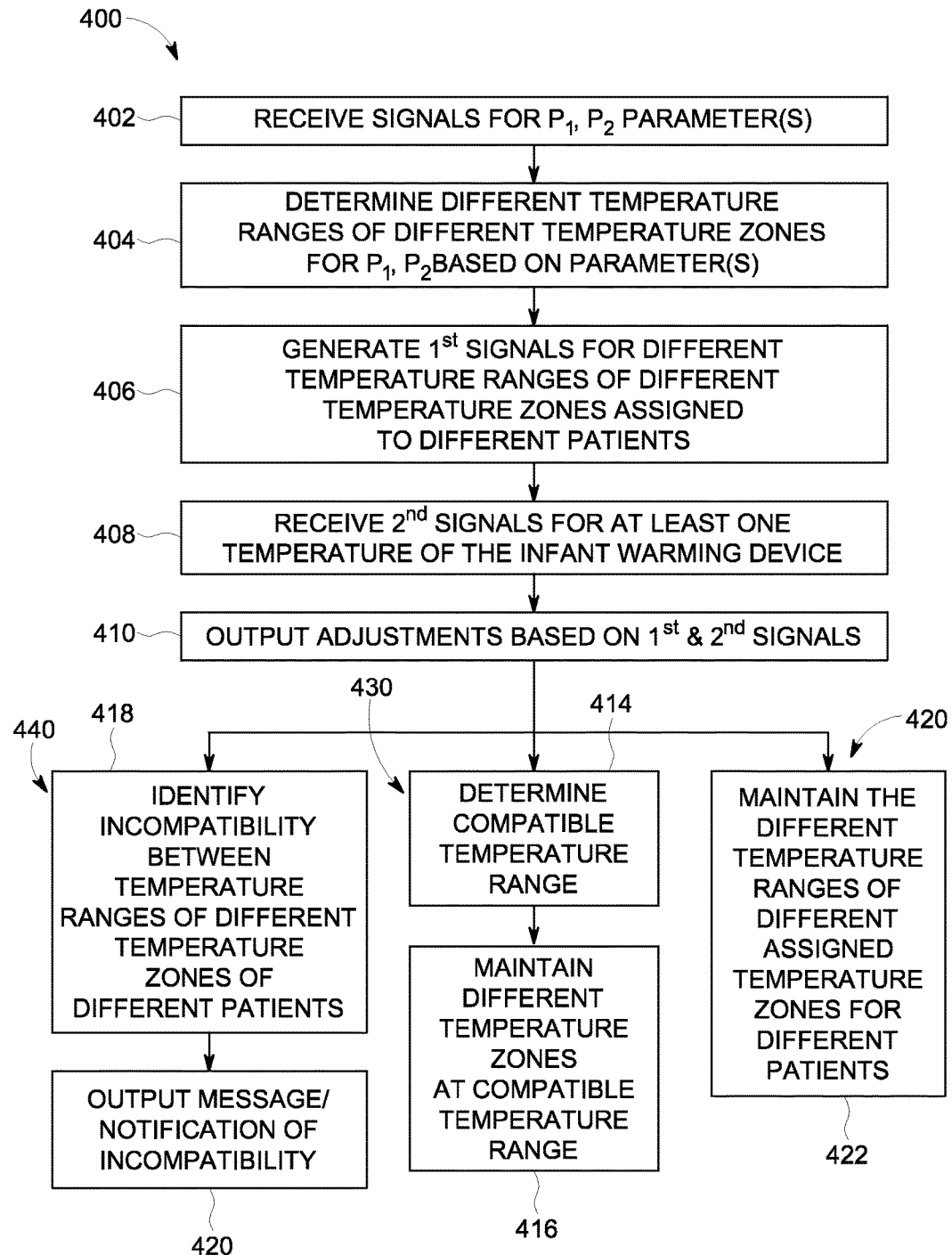
FIG. 5 is a flow diagram of another example method that may be carried out by the system of FIG. 4.

As indicated by step 404 of FIG. 5, controller 374 (processing unit 42 following instructions contained in memory 344) determines the different temperature ranges for the different temperature zones for each of the patients based upon the signals for the different parameters received in step 402. For example, in circumstances where warming chamber 24 has two temperature zones 36, 38 about patients P1, P2, respectively, controller 374 determines a first temperature range for the first zone 36 and a second, possibly different, temperature range for the second zone 38. Such temperature ranges may be determined based upon one or more of the signals received a step 402 such as the weight, blood oxygen saturation level, length, gestational age and session or other specific health conditions for each of the patients within warming chamber 24. In one implementation, controller 374 may present recommended temperature ranges for each of patients P1, P2 and message device 374, requesting confirmation or allowing adjustment by a care person. As indicated by step 406, processing unit 42 generates first signals for the different temperature ranges of the different temperature zones assigned to the different patients within warming chamber 24. The signals are utilized to store the determined temperature ranges within memory 344 and for use in the management of warming device 22.

As illustrated by FIG. 5, the output of adjustments in step 410 based on the first and second signals occurs with management system 320 operating in one of three user or care person selectable modes: (A) a dedicated temperature zone maintenance mode 420, (B) a compatible temperature zone maintenance mode 430; and (C) a compatibility notification mode 440. The individual mode or modes are selectable by the care person using input 30, wherein the selected mode or modes are stored in memory 344. In yet other implementations, system 320 may alternatively operate in a greater or fewer number of such selectable modes. In one implementation, system 320 is operated in only one of the three illustrated modes.

A. Dedicated Temperature Zone Maintenance Mode

As indicated by step 422, when in the dedicated temperature zone maintenance mode 420, controller 374 maintains the different temperature ranges of the different assigned temperature zones 36, 38 for the different patients P1, P2. In particular, using the determined temperature ranges for each of the temperature zones 36, 38, stored in memory 44, and using the current sensed temperatures for each of zones 36, 38 received in step 408, controller 374 generates control signals adjusting the heating by heating devices 364, 366 and/or the cooling provided by cooling device 368, 370 such that each of temperature zones 36, 38 is maintained within the temperature range determined for the particular temperature zone 36, 38 in step 404. In implementations where the recommended temperature range for each of the different temperature zones 36, 38 is itself based upon sensed parameters providing dynamic feedback, such as the current weight of each of the individual patients P1, P2, the current positioning of the patients P1, P2 and the blood oxygen saturation level of each of patients P1, P2, controller 374 dynamically adjusts the different temperature ranges for the different temperature zones 36, 38 continuously or at predefined periodic intervals, which may also result in the generation of control signals adjusting the operation of heating devices 364, 366 and cooling devices 368, 370 to satisfy the dynamically changing temperature ranges or the dynamically changing boundaries of the temperature zones 36, 38.

In circumstances where warming chamber 24 contains greater than two patients and includes more than two different temperature ranges for more than two different temperature zones, controller 374 may generate control signals causing message device 372 to output a recommendation that two of the patients within the warming device be switched with respect to one another such that there associated temperature zones are also relocated to increase the compatibility of the temperature ranges of adjacent temperature zones. As a result, temperature gradients between adjacent temperature zones are reduced, enhancing the ability of controller 374 to independently adjust the heating and/or cooling of adjacent temperature zones so as to satisfy the determined temperature ranges for the adjacent temperature zones. In other words, there is a reduced likelihood that heat from a temperature zone having a higher temperature range will inadvertently raise the temperature of an adjacent temperature zone having a lower temperature range.

B. Compatible Zone Temperature Maintenance Mode

As indicated by step 414, when controller 374 is operating in the compatible zone temperature maintenance mode, controller 374 determines a compatible temperature range, a temperature range that is compatible with both the first determined temperature range for the first temperature zone 36 and the second determined temperature range for the second temperature zone 38. When in the compatible zone temperature maintenance mode, controller 374 facilitate the maintenance of both zones 36, 38 at a single common temperature or within a single common range of temperatures. The compatible zone temperature maintenance mode facilitates use of system 320 when system 320 lacks ability to independently vary the temperature of each of temperature zones 36, 38, such as when independently adjustable heaters or cooling devices are not provided or such as when one or more of such independently variable or controllable heating or cooling devices are inoperable.

Figure 6:
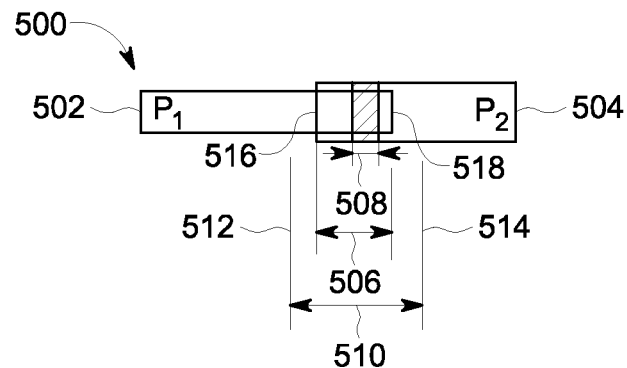
FIG. 6 is a diagram of an example display of compatible temperature ranges that may be presented by the system of FIG. 4.

FIG. 6 illustrates an example of a display 500 that may be presented by message device 322 when system 320 is operating in the compatible zone temperature maintenance mode. As shown by FIG. 6, controller 374 (processing unit 42 following instructions contained memory 344) generates control signals causing message device 372 to present a graphic 502 graphically representing the determined recommended temperature range for temperature zone 36 and graphic 504 representing the determined recommended temperature range for temperature zone 38 as determined in step 404. In the example illustrated, the temperature ranges represented by graphics 502, 504 overlap.

As further indicated by FIG. 6, controller 374 generates control signals causing message device 372 to identify different selectable temperature ranges that are compatible to the temperature ranges as determined in step 404. In the example illustrated, controller 374 graphically identifies a first selectable compatible temperature range 506 comprising the overlapping portions of the ranges indicated by graphics 502, 504. Controller 374 graphically identifies a second selectable compatible temperature range 508 which is a sub range of temperature range 506. In one implementation, temperature range 508 may comprise a narrower optimum temperature range that is recommended for accommodating the different temperature ranges indicated by graphics 502, 504.

In the example illustrated, controller 374 further graphically identifies a third selectable compatible temperature range 510 which extends outside of or beyond range 506 in at least one direction. In some circumstances, each or one of patients P1, P2 may be tolerant of temperatures outside the temperature range determined and assigned to the particular patient. Range 510 is based upon such tolerance levels for patients P1, P2, providing an even larger compatible temperature range. Although the lowermost temperature 512 and the uppermost temperature 514 of temperature range 510 are illustrated as being equally spaced from the lowermost temperature 516 of the temperature range indicated by graphic 504 and the uppermost temperature 518 of the temperature range indicated by graphic 502, indicating an equal amount of tolerance for each of patients P1 and P2 to temperature is outside of their recommended temperature ranges, in other circumstances, the lowermost temperature 512 and the uppermost temperature 514 may have other values. For example, in circumstances where patient P2 has zero tolerance for temperatures outside of the associated recommended range indicated by graphic 504, the lowermost temperature 512 may correspond to the lowermost temperature 516 of the range indicated by graphic 504. In circumstances where patient P1 has an even greater tolerance for temperatures outside of the recommended temperature range indicated by graphic 502, the uppermost temperature 514 of range 510 may be located even further to the right of the uppermost temperature 518 of the temperature range indicated by graphic 502. In circumstances where patient P2 has an even greater tolerance for temperatures outside of the recommended temperature range indicated by graphic 502, the lowermost temperature 512 of range 510 may be located even further to the left of the lowermost temperature 516 of the temperature range indicated by graphic 504.

In one implementation, controller 374 prompts the care person to select a temperature within the determined compatible temperature range. In one implementation, controller 374 prompts the care person to select one of the graphically depicted compatible temperature ranges presented on message device 372 for use in maintaining a temperature of warming compartment 24. In some implementations, controller 374 generates control signals causing message device 372 to present a graphical user interface such as a slider bar or cursor, that allows the care person to manually adjust the extent of the range such as by manually sliding or moving one or both of the uppermost temperature or the lowermost temperature of a particular compatible temperature range to the left or to the right. As indicated by step 416, once the compatible temperature range has been either determined and/or selected by the care person, controller 374 maintains both temperature zones 36, 38 at one or more temperatures within the compatible temperature range. In one implementation, controller 374 receive signals from sensor 26, 28 indicating the current temperature of zones 36, 38 within chamber 24 and generates control signals adjusting heaters 364, 366 and/or cooling devices 368, 370 to maintain temperature zones 36, 38 at one or more temperatures within the compatible temperature range. In implementations where system 420 operates under the compatible temperature zone maintenance mode, the determination and/or use of temperature zones 36, 38 may be omitted since the entirety warming chamber 24 is maintained at a single temperature or a temperature satisfying a single temperature range.

C. Compatibility Notification Mode

As indicated by step 418, when operating in the compatibility notification mode, controller 374 identifies incompatibility between the temperature ranges of the different temperature zones 36, 38 of different patients P1, P2 as determined in step 404. In one implementation, two temperature ranges of different temperature zones are incompatible when the temperature of each of the zone 36, 38 cannot be maintained at a temperature falling within the temperature range assigned to determine for each zone 36, 38. In implementations where system 320 does not have the capability to independently heat and/or cool to temperature zone 36, 38, an incompatibility may occur when controller 374 determines that there is not a single temperature or a single temperature range at which warming chamber 24 may be maintained that will satisfy the individual temperature range requirements for temperature zones 36, 38 and for patients P1, P2, respectively. In implementations where system 320 does have the capability to independently varying control the temperature of temper zone 36, 38 by independently controlling the operation of heating devices 364, 366 and/or cooling devices 368, 370, an incompatibility may still occur when controller 374 determines that the determined temperature ranges for the different adjacent temperature zones are sufficiently disparate such that heat from one temperature zone 36, 38 of flow into the other adjacent temperature zone 36, 38 such that even with independent heating and cooling, both temperature zones 36, 38 may not be maintained at temperatures within the determined temperature ranges for the zones 36, 38. As noted above, in implementations where system 320 lacks ability to independently heat and/or cool temperature zones 36, 38, the determination of such zones 36, 30 may be omitted. In such implementations, controller 374 identifies an incompatibility as when the recommended or at least acceptable temperature ranges (either determined for each of patients P1, P2 or input as a selection by a care person through input 30) for each of patients P1, P2 cannot be both satisfied.

As indicated by step 420, in response to determining an incompatibility between the temperature ranges of different temperature zones (or of different patients cohabitating warming device 24), controller 374 generates control signals causing message device 372 to output a message/notification of incompatibility. In one implementation, the "message" may comprise an audible or visible alert or notification such as an illuminated warning light, a flashing light, and audible beep or other sound, or an audible repeated word such as "warning, incompatibility". In another implementation, the message may additionally or alternatively comprise a textual message warning of the compatibility and comprising a recommendation for addressing the incompatibility. For example, the message may comprise recommendation that the care person remove one of patients P1, P2 from warming chamber 24.

Figure 7:
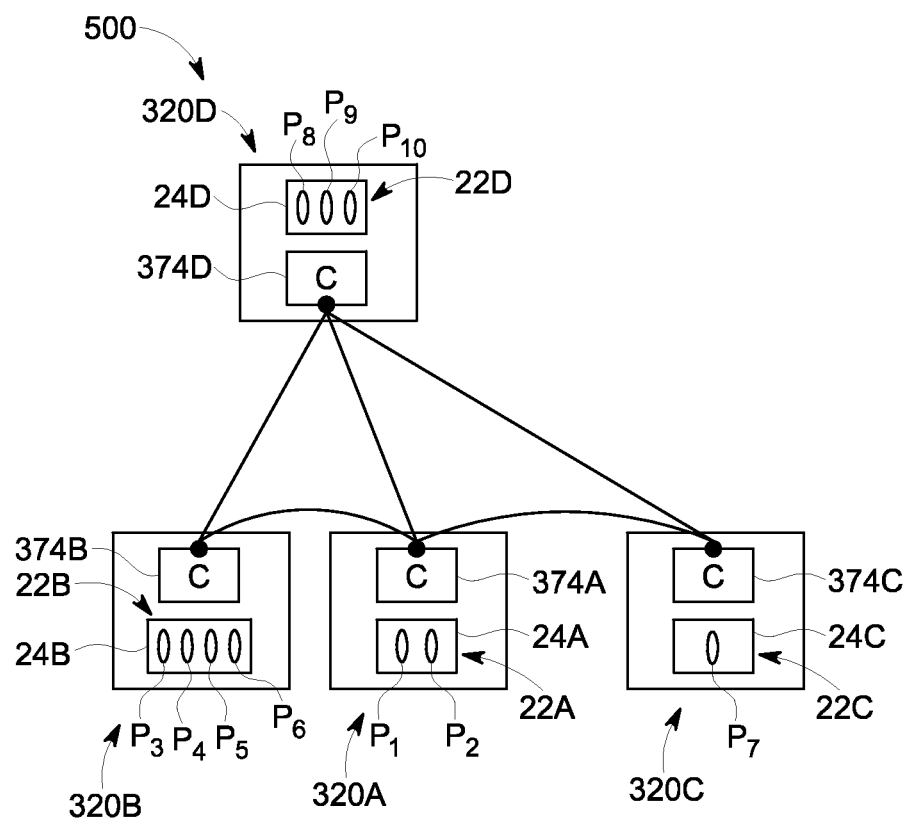
FIG. 7 is a schematic diagram of an example infant care facility comprising a plurality of the management systems of FIG. 4.

FIG. 7 illustrates an example infant warming facility 500, such as a neonatal healthcare unit, comprising multiple infant warming management systems 320A, 320B, 320C and 320D (collectively referred to as infant warming management systems 320). Infant warming management systems 320 are each similar to infant management warming system 320 described in FIGS. 4 and 5. Infant warming management systems 320A, 320B, 320C and 320D comprise infant warming devices 22A, 22B, 22C, 22D (collectively referred to as infant warming devices 22) having infant warming chambers 24A, 24B, 24C, 24D (collectively referred to as chambers 24); and infant warming device managers or controllers 374A, 374B, 374C and 374D (collectively referred to as controllers 374), respectively. In one implementation, each of infant warming management systems 320 shown in FIG. 6 additionally comprise each of the components shown and described above with respect to infant warming manager system 320 of FIG. 4.

As shown by FIG. 7, warming chambers 24 of systems 320 may, at a particular time, contain different numbers of patients. In some implementations, different warming chambers 24 of different systems 320 may have different sizes so as to contain different numbers of patients. In some implementations, different systems 320 may have different capabilities. For example, in one implementation, one or more of systems 320 may omit the capability to independently vary or control the heating and/or cooling of individual temperature zones within a single warming chamber 24. In some implementations, one or more systems 320 may be configured to operate in less than all of the three operational modes described with respect to FIG. 5. In the example illustrated, warming chamber 24A is illustrated as receiving patients P1, P2, warming chamber 24B is illustrated as receiving patients P3, P4, P5 and P6, warming chamber 24C is illustrated as receiving a single patient P7, and warming chamber 24D is illustrated as receiving patients P8, P9 and P10.

In the example illustrated, each of systems 320 is configured to communicate with one another. In one implementation, each of systems 320 communicates with other systems 320 in a wired fashion. In one implementation, each of systems 320 communicates with other systems 320 directly in a wireless fashion. In yet another implementation, each of systems 320 communicates with other systems 320 in a wired or wireless fashion across an intermediary such as the across a local area network or a wide area network such as the Internet.

In the example implementation shown in FIG. 7, when in the incompatibility notification mode 440 (shown in FIG. 5), controllers 374 communicate identified incompatibilities to one another, the different temperature ranges of different temperature zones that are being maintained at each of the warming chambers 24 and available space, if any for each of warming chambers 24. Based upon identified incompatibilities, available space and/or current temperature ranges being maintained, a designated one of controllers 374 determines whether a particular patient at any one of systems 320 should be relocated to a different one of systems 320 that may offer a more compatible temperature or temperature range for the particular patient. Controller 374 determines which other of systems 320 the particular patient should be relocated to and outputs the recommended relocation location as part of the message that is output in step 420 in FIG. 5.

In one circumstance, the designated controller may recommend that a patient be removed from one of warming chambers 24 and added to a different one of warming chambers 24 having sufficient space. For example, controller 374D may determine that patient P10 has an associated determined temperature range that is incompatible with the determined temperature ranges of patients P8 or P9. Controller 374D may also receive signals indicating that infant warming chamber 24C has available space and is operating or is being maintained at a temperature that would be compatible with the temperature range recommended for patient P10. In such a circumstance, controller 374 generates control signals causing message device 372 (shown in FIG. 4) of one or both of systems 320C or 320D to present a message recommending that patient P10 be removed from warming chamber 24D in place within warming chamber 24C.

In one circumstance, the designated controller 374 may recommend that two patients be switched. For example, controller 374D (the designated controller) may receive signals from controller 374B indicating that patient P4 has a temperature range that is incompatible with the temperature ranges of patients P3, P5 and/or P6. Controller 374D may also receive signals from controller 374A indicating that patient P1 has a temperature range that is incompatible with the temperature range of patient P2. In such a circumstance, controller 374 generates control signals causing message device 372 of one or both of systems 320A and/or 320B to present a message recommending that patient P4 be switched with patient P1.

In yet another implementation, the designated controller 374 is configured to output a recommended cohabitation location for an infant prior to the infant being initially placed within one of warming chambers 24. For example, in one implementation, the designated controller 374 prompts for information or retrieves information regarding a to be placed infant, such as the weight, age, size and/or health conditions of the infant. Based upon such information, the designated controller 374 determines a recommended temperature range for the to be placed infant. Using the determined recommended temperature range for the to be placed infant, the designated controller 374 evaluates each of the current operational settings for warming chambers 24, existing space within warming chambers 24 and/or the recommended temperature ranges for the infants residing in warming chambers 24 to determine in which of warming chambers 24 an infant should be placed. The determination and associated recommendation is then presented on a display or other output device. In some circumstances, the designated controller 374 may recommend that an infant currently residing in one of warming chambers 24 be moved to a different warming chamber 24 to make space for a to be placed infant. In some circumstances, designated controller 374 may recommend that the to be placed infant be placed in a currently empty warming chamber 24 or that an infant currently residing in a warming chamber be moved to empty or otherwise make space in the warming chamber for receiving the to be placed infant.

In one implementation, designated controller 374 may additionally determine a recommended warming chamber location for a to be placed infant based upon a user input or controller retrieved arrival schedule of incoming infants (anticipated future delivery times or other times that additional infants are estimated to arrive at facility 500). In one implementation, designated controller 374 may additionally output the determination of the recommended warming chamber location for a to be placed patient or infant based upon the expected or anticipated health condition and/or expected temperature range requirements for the future incoming infants. In one implementation, designated controller 374, based upon characteristics of the current infants residing warming chambers 24 and based upon the expected or anticipated timing and/or health conditions for newly arriving infants may determine and output a schedule for infant cohabitation or placement in the various warming chambers 24. In such a manner, the designated controller 374 facilitates the preemptive relocation of existing infants amongst the various warming chambers 24 prior to the anticipated arrival of a newly delivered infant, allowing the warming chamber designated for the anticipated arrival of the newly delivered infant to be cleaned and/or otherwise prepared and made ready.

Figure 8:
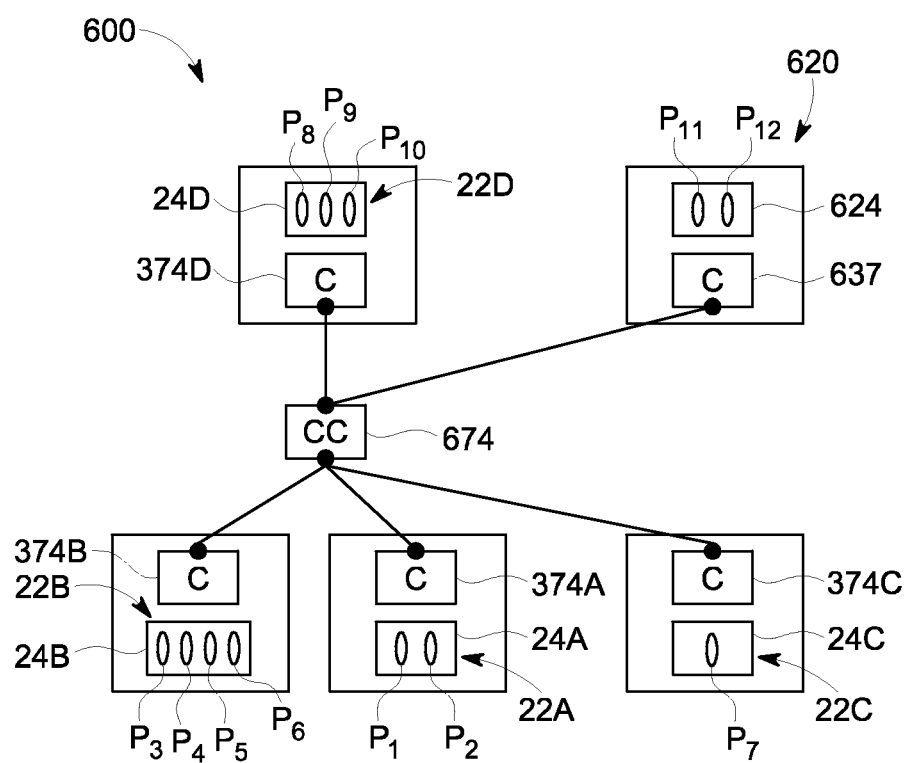
FIG. 8 is a schematic diagram of another example infant care facility.

FIG. 8 schematically illustrates facility 600, another example implementation of facility 500. Facility 600 similar to facility 500 except that facility 600 additionally comprises an independent compatibility controller 674. Compatibility controller 674 comprises a computing device independent of each of systems 320. Compatibility controller 674 communicates with each of systems 320. Compatibility controller 674 receive signals from each of systems 320 indicating the number of patients or the temperature zones of the warming devices of each of systems 320, the temperatures or temperature ranges in which the different temperature zones are being maintained and any incompatibility between patient temperatures or temperature ranges as determined by the controllers 374 of the individual systems 320. Based upon such signals, compatibility controller 674 (comprising a processor following instructions contained in a non-transitory computer-readable medium) identifies recommended relocations or switching of patients amongst the different warming chambers 24 to reduce or eliminate patient or temperature range incompatibilities and/or to achieve more compatible adjacent temperature zones or a lower temperature gradient across adjacent different temperature zones within individual warming chambers 24. Based upon the identified relocation or switching recommendation, controller 674 generates control signals causing a message device associated with controller 674 or a message device of one or more of systems 320 to display or otherwise output a relocation or switching recommendation.

As further shown by FIG. 7, in another implementation, controller 674 may additionally carry out method 400 shown in FIG. 5 for one or more of warming devices 22 in lieu of the particular controller 374 associated with each particular warming device 22. In the example illustrated, facility 600 includes a system 620 having an infant warming device 624 under the control of a controller 637. Controller 637 lacks the programming or one or more of the components for carrying out method 200 and/or method 400. As a result, controller 674 may provide the benefits of method 400 to infant warming device 624 in facility 600. In one implementation, facility 600 may at least almost entirely comprise infant warming devices lacking an infant warming device managing controller 374. In such an implementation, controller 674 may be added to facility 600 to identify incompatibilities, to provide notice of such temperature range incompatibilities and/or output recommendations for patient relocations or switching to lessen temperature range incompatibilities.

In one implementation, controller 674 resides within facility 600, communicating directly with each of systems 320, 620 in a wired or wireless fashion. In yet another implementation, controller 674 resides remote from facility 600 and remote from each of systems 320, 620. For example, controller 674 may reside at a remote location and communicate with systems 320, 620 in a wired or wireless fashion across a local area network or a wide area network such as the Internet. In one implementation, controller 674 may be provided by a remote server.

Figure 9:
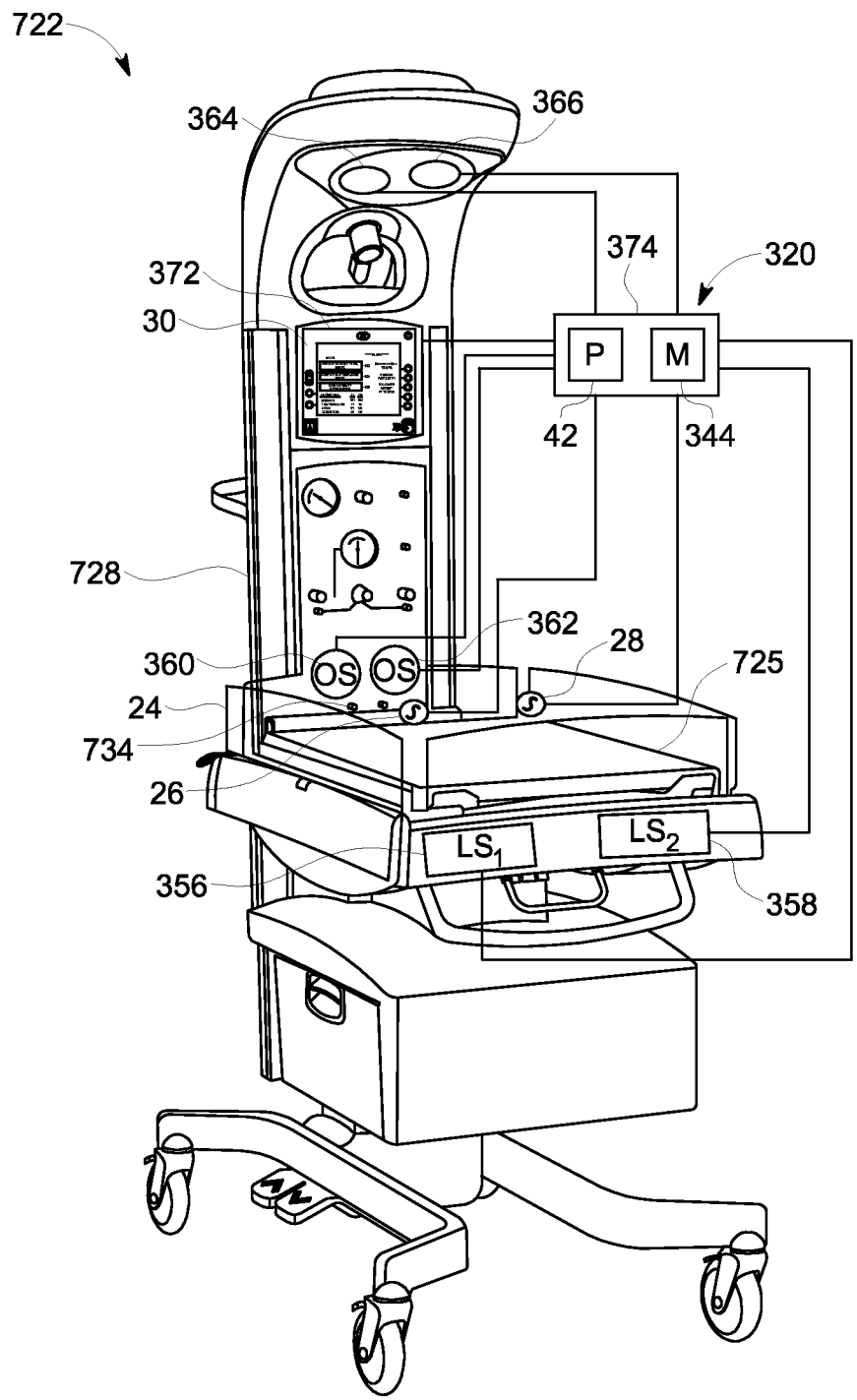
FIG. 9 is a perspective view of an example infant warming device incorporating the management system of FIG. 4.
Figure 10:
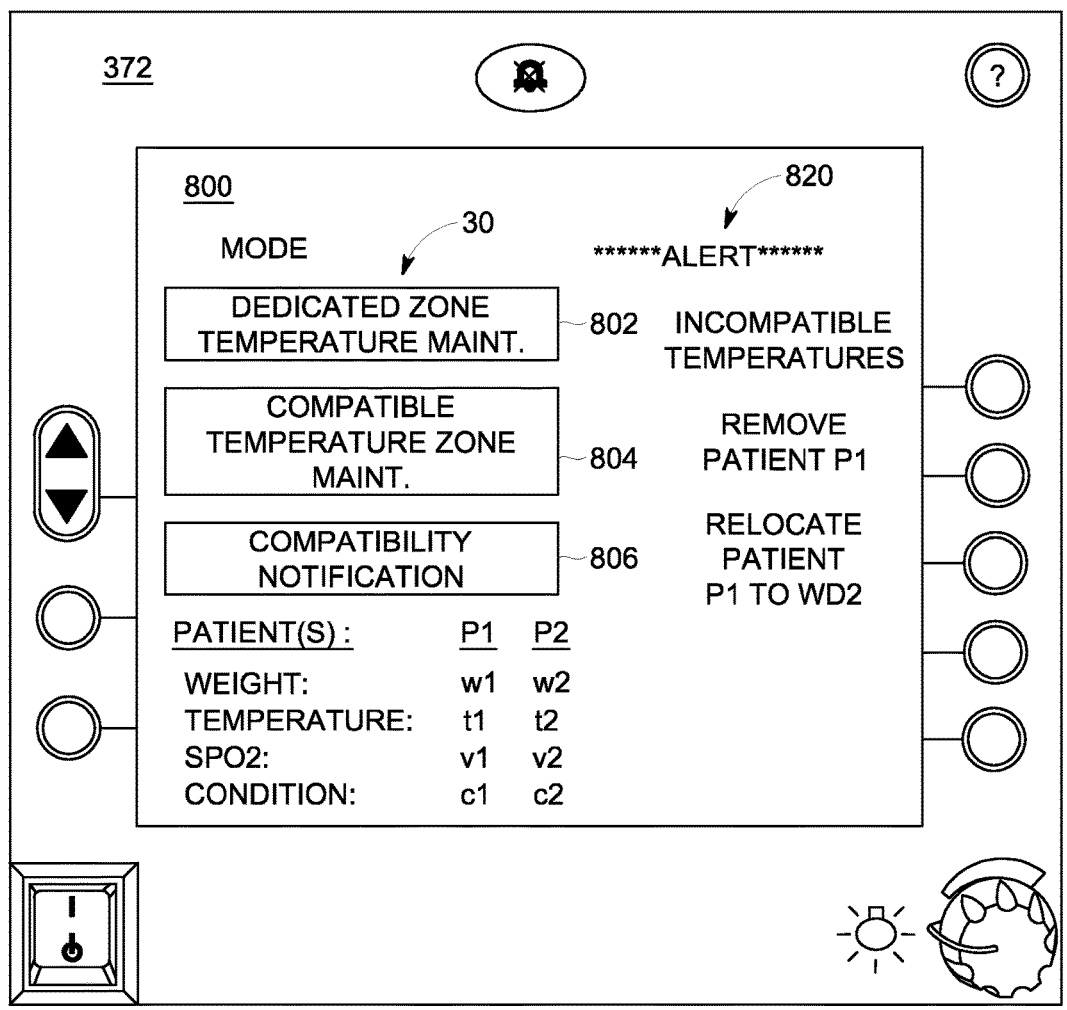
FIG. 10 is a front view of an example display presented by a message device of the infant warming device management system of FIG. 8.

FIGS. 9 and 10 illustrate multi-patient infant warming device management system 320 incorporated as part of a warming device 722, an implementation of warming device 22. Those components of infant warming device management system 320 depicted in FIG. 9 that correspond to components of system 320 shown in FIG. 4 are numbered similarly. As shown by FIG. 9, warming device 722 comprises warming chamber 24 in the form of a crib having a mattress 725. Underlying mattress 725 are load sensors 356, 358. As noted above, in some implementations, load sensors 356, 358 may have various configurations such as an array of individual load sensors.

As further shown by FIG. 9, infant warming device 722 further comprises a neck 728 which rises above warming chamber 724 and supports optical sensors 360, 362, heating devices 364, 366, input 30, message device 372 and controller 374 (schematically shown to the side of neck 728. Neck 728 further comprises receptacles or ports for receiving plugs associated with sensors 26, 28. In the example illustrated, heating devices 364, 366 comprise radiant heating devices supported overhead of warming chamber 24 by neck 728. Each of heating devices 364, 366 is configured to aim or focus heat on to a particular area or region of compartment chamber 24 to provide independently controllable and varying temperature zones. In other implementations, heating device 722 may comprise a single radiant heating device for heating chamber 24 to a single temperature.

Input 30 and message device 372 are supported by neck 728. Input device 30 comprises one or more pushbuttons. In one implementation input device 30 additionally comprises graphical user interfaces provided on message device 372, comprising a touch screen. Sensors 26, 28 comprise sensors that attach or mount to individual patients within warming chamber 24. In the example illustrated, sensors 26, 28 (schematically shown) plug into ports 734 to communicate with controller 374. Sensors 26, 28 sense the temperature of the individual patients within warming chamber 24. In other implementations, sensors 26 and 28 or alternatively supported adjacent to portions of warming chamber 24 to sense the air temperature about the individual patients within warming chamber 24.

Controller 374 is described above with respect to FIG. 4. As noted above, in one implementation, controller 374 is configured to carry out method 400 described in FIG. 5. In another implementation, controller 374 is configured to carry out method 100 or method 200 described above with respect to FIGS. 2 and 3, respectively. FIG. 10 illustrates an example display 800 presented by message device 372 of infant warming device 722 and system 320. As shown by FIG. 10, controller 374 generates control signals causing device 372 to present display 800. Display 800 includes three selectable graphical user interfaces for the three modes of system 320: a dedicated zone temperature maintenance mode GUI 802, a compatible temperature zone maintenance mode GUI 804 and a compatibility notification mode GUI 806. Each of the GUIs is selectable by a care person through the use of a mouse and pointer or with touch in the case of a touch screen. In one implementation, upon being selected, the graphical user interface 802, 804, 806 changes color, brightness or other characteristics to distinguish itself from the other unselected GUIs to indicate its selection.

As further shown by FIG. 10, display 800 identifies the current patients residing or cohabitating within warming chamber 24 based upon either input by the care person through input 30 or as detected by load sensors 356, 358 and/or optical sensors 360, 362. For each of the patients P1, P2 within warming chamber 24, displayed 800 provides values for the parameters for each of such patients such as each patient's determined or care person inputted weight (w1, w2), each patient's determined or inputted temperature or temperature range (t1, t2), each patient's sensed blood oxygen saturation level (SPO2) (v1, v2) and any additional inputted or sensed condition for each patient (c1, c2). In one implementation, display 800 may additionally display the actual existing temperature of each of patients P1, P2.

FIG. 10 illustrates system 320 operating in the compatibility notification mode. In the example illustrated, controller 374 has identified an incompatibility between the determined or input temperature zones of patients P1 and P2. As a result, controller 374 generates control signals causing the notification message 820 to be presented. Notification message 820 comprises an illuminated or flashing alert to catch the attention of a care person. Message 820 further provides an illuminated indication that there are incompatible temperature zones within warming chamber 24. In the example illustrated, message 820 further recommends that patient P1 be removed and relocated to a particular different warming device, warming device WD2. In implementations where warming device 722 is not part of a larger facility or where controller 374 does not communicate with other warming devices, the recommendation for relocating the patient to a other specifically identified warming device may be omitted.

In other implementations, message 820 may have other layouts as well as other content. In other implementations, message device 372 may have other configurations. Likewise, in other implementations, warming device 722 may have other configurations. For example, in other implementations come warming device 722 may comprise an infant care station, a different infant warmer, an incubator, a hybrid warmer/incubator or other patient care stations in which multiple cohabitating infants are to be concurrently warmed.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A multiple patient infant warming device comprising:
a computer processor;
an input device operatively connected to the computer processor;
a plurality of dedicated temperature zones within the infant warming device, each dedicated temperature zone assigned to a different one of a multiple of patients;
a plurality of temperature sensors operatively connected to the computer processor, wherein each dedicated temperature zone is associated with one of the plurality of temperature sensors;
a plurality of temperature regulating devices that each heat or cool a portion of the infant warming device, wherein each dedicated temperature zone is associated with one of the plurality of temperature regulating devices;
wherein the computer processor is configured to:
determine a temperature range for each of the plurality of dedicated temperature zones based on data from one of the input device and the plurality of temperature sensors; and
control the plurality of temperature regulating devices to maintain each dedicated temperature zone within the respective temperature range.

2. The multiple patient infant warming device of claim 1, wherein the computer processor is configured to calculate the temperature range for each of the plurality of dedicated temperature zones based on data from the input device, wherein the data from the input device comprises a patient weight for each of the multiple patients.

3. The multiple patient infant warming device of claim 1, wherein the computer processor is configured to calculate the temperature range for each of the plurality of dedicated temperature zones based on data from the input device, wherein the data from the input device comprises a patient age for each of the multiple patients.

4. The multiple patient infant warming device of claim 1, wherein the computer processor is configured to maintain the dedicated temperature zone for each of the multiple patients within the respective temperature range based on feedback from the plurality of temperature sensors.

5. The multiple patient infant warming device of claim 1, wherein the computer processor is configured to identify any patient incompatibility between temperature ranges of the dedicated temperature zones assigned to different ones of the multiple patients based on data from the input device.

6. The multiple patient infant warming device of claim 5, wherein the computer processor is configured to generate an alarm based on an identified patient incompatibility.

7. The multiple patient infant warming device of claim 6, further comprising a display operatively connected to the computer processor.

8. The multiple patient infant warming device of claim 7, wherein the computer processor is configured to generate an infant placement recommendation based on the identified patient incompatibility, and wherein the display is configured to communicate the infant placement recommendation.

9. The multiple patient infant warming device of claim 1, wherein the computer processor is configured to control each of the plurality of temperature regulating devices based on the temperature range for the associated dedicated temperature zone and the temperature range for an adjacent dedicated temperature zone.

10. The multiple patient infant warming device of claim 9, wherein the computer processor is further configured to determine a temperature gradient between adjacent dedicated temperature zones, and to control each of the plurality of temperature regulating devices based on the temperature gradient.

11. A multiple patient infant warming management system comprising:
at least two temperature sensors for sensing at least two temperatures within an infant warming device, wherein each temperature is measured in a different temperature zone assigned to different patients of a multiple of patients to be concurrently warmed in the infant warming device;
a controller operatively connected to the at least two temperature sensors, the controller configured to:
process first signals for different temperature ranges associated with the different temperature zones assigned to the different patients;
receive second signals from each of the at least two temperature sensors indicating at least one temperature in the respective temperature zone of the infant warming device; and
control at least one heating device or one cooling device for each temperature zone based on the first signals and the second signals to maintain each temperature zone within the respective temperature range.

12. The multiple patient infant warming management system of claim 11, wherein the at least two temperature sensors include at least one temperature sensor for each of the different patients to be warmed by the infant warming device.

13. The multiple patient infant warming management system of claim 11, wherein the controller is further configured to determine the different temperature ranges of the different temperature zones and to generate the first signals.

14. The multiple patient infant warming management system of claim 13, wherein the determining of the different temperature ranges of the different temperature zones is based on a parameter selected from a group of parameters consisting of: a patient weight for each of the different patients; a temperature of each of the different patients; a patient age for each of the different patients; and an oxygen concentration of each of the different patients.

15. The multiple patient infant warming management system of claim 13, wherein the determining of the different temperature ranges of the different temperature zones is based on the second signals.

16. The multiple patient infant warming management system of claim 11, wherein the controller is configured to operate in one of a plurality of care person selectable modes comprising:
a dedicated temperature zone maintenance mode in which the controller generates control signals to maintain the different temperature ranges of the different temperature zones assigned to the different patients;
a compatible temperature zone maintenance mode in which the controller (a) determines a compatible temperature range compatible to a plurality of the different temperature ranges of the different temperature zones assigned to the different patients and (b) generates control signals to maintain the different temperature zones within the compatible temperature range; and
a compatibility notification mode in which the controller (a) identifies incompatibility between the different temperature ranges of the different temperature zones assigned to the different patients and (b) outputs a message based upon the identified incompatibility.

17. The multiple patient infant warming management system of claim 11, wherein the controller is further configured to output adjustments based on the first signals and the second signals is selected from a group of adjustments consisting of: (1) generating control signals to maintain the different temperature ranges of the different temperature zones assigned to the different patients; (2) determining a compatible temperature range compatible to a plurality of the different temperature ranges of the different temperature zones assigned to the different patients and generating control signals to maintain the different temperature zones within compatible temperature range; and (3) identifying incompatibility between the different temperature ranges of the different temperature zones assigned to the different patients and outputting a message based upon the identified incompatibility.

18. The multiple patient infant warming management system of claim 11, wherein the at least two temperature sensors includes at least one temperature sensor for each of the different patients and wherein the controller is further configured to control the at least one heating device or cooling device for each temperature zone by generating control signals to maintain the different temperature ranges of the different temperature zones assigned to the different patients based on feedback from the at least one temperature sensor for each of the different patients.

19. The multiple patient infant warming management system of claim 11, wherein the controller is further configured to determine a compatible temperature range compatible to the different temperature ranges of the different temperature zones assigned to the different patients and wherein the controller is further configured to control the at least one heating device or cooling device for each temperature zone by generating control signals to maintain the different temperature zones within the compatible temperature range.

20. The multiple patient infant warming management system of claim 11, wherein the controller is further configured to identify incompatibility between the different temperature ranges of the different temperature zones assigned to the different patients and output a message based on the identified incompatibility.

21. The multiple patient infant warming management system of claim 20, wherein the message comprises an alarm based on the identified incompatibility.

22. The multiple patient infant warming management system of claim 20, wherein the message comprises an infant placement recommendation based on the identified incompatibility.

23. The multiple patient infant warming management system of claim 11 further comprising a presence sensor to output signals;
wherein the controller is configured to determine a number of patients to be concurrently warmed by the warming device.

24. The multiple patient infant warming management system of claim 23, wherein the presence sensor comprises at least one load sensor.

25. The multiple patient infant warming management system of claim 23, wherein the presence sensor comprises at least one optical sensor.

26. A multiple patient infant warming management system comprising:
at least one temperature sensor for sensing at least one temperature of an infant warming device;
a controller operatively connected to the at least one temperature sensor, the controller configured to:
process first signals for different temperature ranges of different temperature zones assigned to different patients to be concurrently warmed in the infant warming device;
receive second signals from the at least one temperature sensor indicating at least one temperature of the infant warming device;
output adjustments based on the first signals and the second signals;
receive third signals for different temperature zones assigned to different patients to be concurrently warmed by one or more other infant warming devices; and
output a recommended location for placement of an infant amongst the infant warming device and the one or more other infant warming devices based upon the first signals and the third signals.

27. The multiple patient infant warming management system of claim 26, wherein the controller is further configured to determine and output a schedule of patient placements amongst the infant warming device and the one or more other infant warming devices based upon estimated arrival times of new infants.

* * * * *